United States Patent [19]

Russ et al.

[11] Patent Number: 5,095,753
[45] Date of Patent: Mar. 17, 1992

[54] DEVICE FOR ULTRASONIC TESTING OF A HEAD SCREW INSERTED INTO A COMPONENT

[75] Inventors: Jakob Russ, Römerberg; Filippo D'Annucci, Mannheim, both of Fed. Rep. of Germany; Jan O. Gustafsson, Järfälla; Staffan Orrgard, Danderyd, both of Sweden

[73] Assignee: ABB Reaktor GmbH, Mannheim, Fed. Rep. of Germany

[21] Appl. No.: 660,711

[22] Filed: Feb. 22, 1991

[30] Foreign Application Priority Data

Feb. 22, 1990 [DE] Fed. Rep. of Germany ....... 4005545

[51] Int. Cl.$^5$ ............................................. G01N 29/04
[52] U.S. Cl. ................................................... 73/598
[58] Field of Search .................. 73/761, 627, 598; 376/245

[56] References Cited

FOREIGN PATENT DOCUMENTS 228345 10/1986 Japan ................................. 73/598
267455 10/1989 Japan ................................. 73/627

Primary Examiner—Jerry W. Myracle
Attorney, Agent, or Firm—Herbert L. Lerner; Laurence A. Greenberg

[57] ABSTRACT

In devices for the ultrasonic testing of a head screw inserted into a component, a skew position of an ultrasonic probe with respect to the screw head leads to inaccurate test results. In order to achieve precise test results independently of the position of the screwing-in axis, at least one ultrasonic transducer is disposed in a cradle-mounted centering piece of the ultrasonic probe. An adaptor of the centering piece is located nearer to the screw head than the ultrasonic transducer. The adaptor is matched to the configuration of the screw head. In order to achieve a centering connection with the screw head, the ultrasonic probe can be moved about its axis and in the axial direction. The device is principally to be used to test screws in the core baffle of a nuclear reactor vessel.

6 Claims, 2 Drawing Sheets

DEVICE FOR ULTRASONIC TESTING OF A HEAD SCREW INSERTED INTO A COMPONENT

The invention relates to a device for ultrasonic testing of a head screw inserted into a component, including an ultrasonic probe facing the end surface of the head of the screw, which can be moved relative to the head of the screw.

Such a device is known from German Patent DE-PS 35 04 522. In that device, an ultrasonic probe is rotated like a planet about a screw axis, and individual segments of the screw head are irradiated ultrasonically one after another. Such operation requires the device to have parts that extend perpendicular to the screw axis and permit the device to be used only under appropriate conditions of space. Furthermore, the stepwise testing results in a long test time. Despite the complicated construction of the device that is necessary for positioning the probe relative to the individual segments, imprecise test results arise in particular, for example, when the screw axis and the probe axis no longer extend parallel to one another because the screwing-in axis deviates from the desired axis.

It is accordingly an object of the invention to provide a device for ultrasonic testing of a head screw inserted into a component, which overcomes the hereinafore-mentioned disadvantages of the heretofore-known devices of this general type and which delivers precise test results in conjunction with a reduced test time independently of the position of the screwing-in axis.

With the foregoing and other objects in view there is provided, in accordance with the invention, a device for ultrasonic testing of a head screw inserted into a component, the screw having a head with an end surface, comprising an ultrasonic probe facing toward the end surface of the head of the screw, the probe having a cradle-mounted centering piece and an axis defining an axial direction, at least one ultrasonic transducer disposed in the centering piece, the centering piece having an adaptor disposed closer to the head of the screw than the at least one ultrasonic transducer, and means for moving the probe about the axis and in the axial direction of the probe for achieving a centering connection with the head of the screw.

The axis of the centering piece which carries the ultrasonic transducers and the screw axis, form a straight line along the imaginary extensions thereof. A precise ultrasonic irradiation takes place in the planned plane independently of the line of the screw axis with respect to the axis of the probe carrier. The rotation which proceeds coaxially with respect to the screw axis takes place only until the centering connection occurs in cooperation with the linear movement of the probe in the axial direction of the screw. The test is then immediately performed. A rotation for the purpose of testing further segments is not required, since an ultrasonic transducer is assigned to the probe for each segment to be tested.

In accordance with another feature of the invention, the screw head has a securing element connected to the component, and the adaptor of the centering piece enters into a centering connection with the securing element alone or in addition to the screw head.

In accordance with a further feature of the invention, the ultrasonic probe is formed of a floating holder, which accommodates the centering piece, is disposed in series therewith, and to which a lift cylinder and a rotary drive are joined in series.

Due to the slim construction of the ultrasonic probe resulting therefrom, it can also be used at narrow locations.

In accordance with an added feature of the invention, there is provided a slip clutch connected between the drive and the lift cylinder, which automatically interrupts the process of rotation after the adaptor has engaged the contour of the screw head.

In accordance with a concomitant feature of the invention, the floating holder overlaps a collar facing away from the screw head, and a compression spring which is extended between the centering piece and the floating holder, is disposed in a cavity in the floating holder, in order to achieving the cradle mounting.

Other features which are considered as characteristic for the invention are set forth in the appended claims.

Although the invention is illustrated and described herein as embodied in a device for ultrasonic testing of a head screw inserted into a component, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawing.

Figure 1:
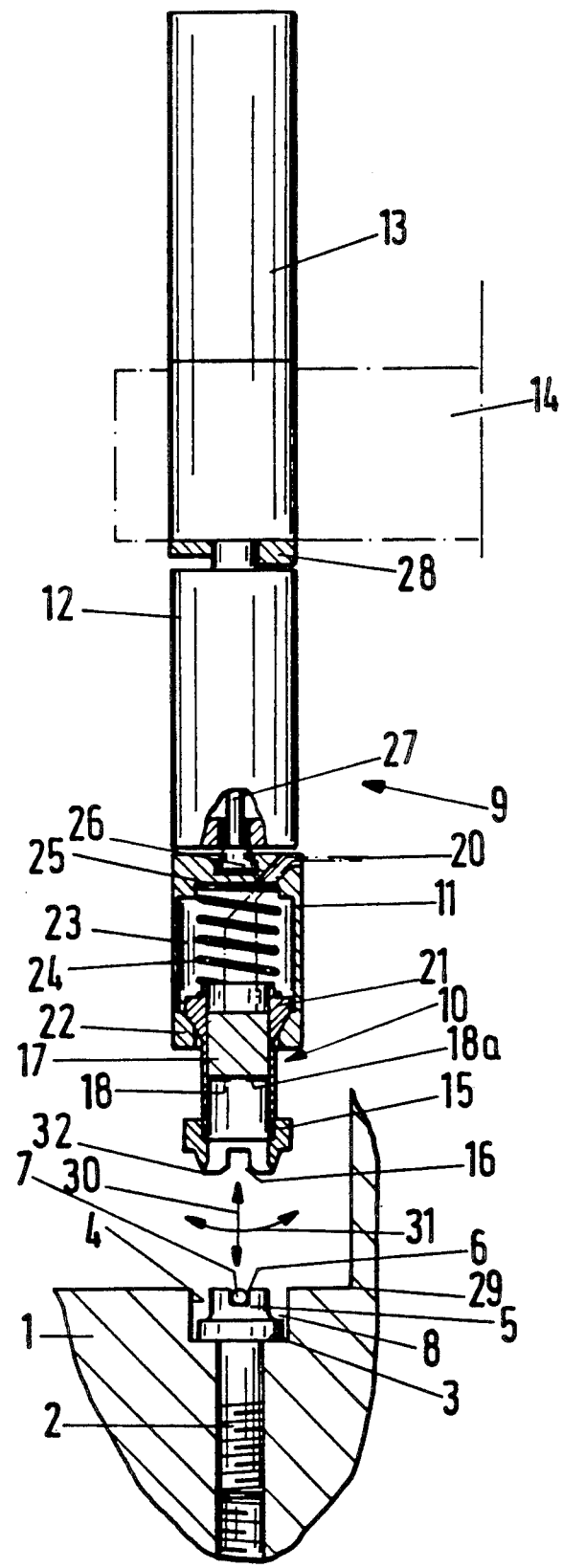
FIG. 1 is a fragmentary, diagrammatic, partly sectional and partly broken-away elevational view of a subregion of a component with a head screw and a probe.
Figure 3:
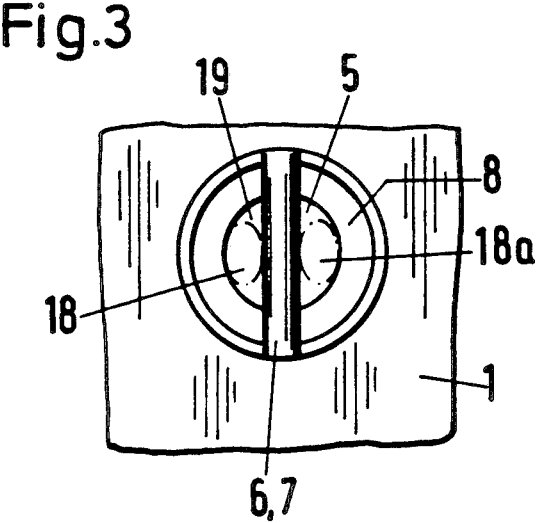
FIG. 3 is a fragmentary view taken along the line III—III of FIG. 2.

Referring now to the figures of the drawing in detail and first, particularly, to FIG. 1 thereof, there is seen a subregion of a component 1, into which a head screw 2 is screwed until its shoulder 3 comes to bear on the floor of a counter bore 4. The head screw 2 has a screw head 5 terminating at the upper edge of the counter bore 4. A securing pin 7, which has a free end that is connected to the component 1 as seen in FIG. 3, extends through a slot 6 in the end surface of the head screw 2. The securing pin 7 thus overreaches or overlaps an annular space 8 formed between the screw head 5 and the counter bore 4.

An ultrasonic probe 9, which is formed of a centering piece 10, a floating or pendulum holder 11, a pneumatic lift cylinder 12 and a rotary drive 13, is inserted in order to test the head screw 2 for cracks. The ultrasonic probe 9 is fastened to a diagrammatically illustrated slide 14, with the aid of which it is brought into the vicinity of the head screw 2 to be tested, as represented in FIG. 1.

Figure 2:
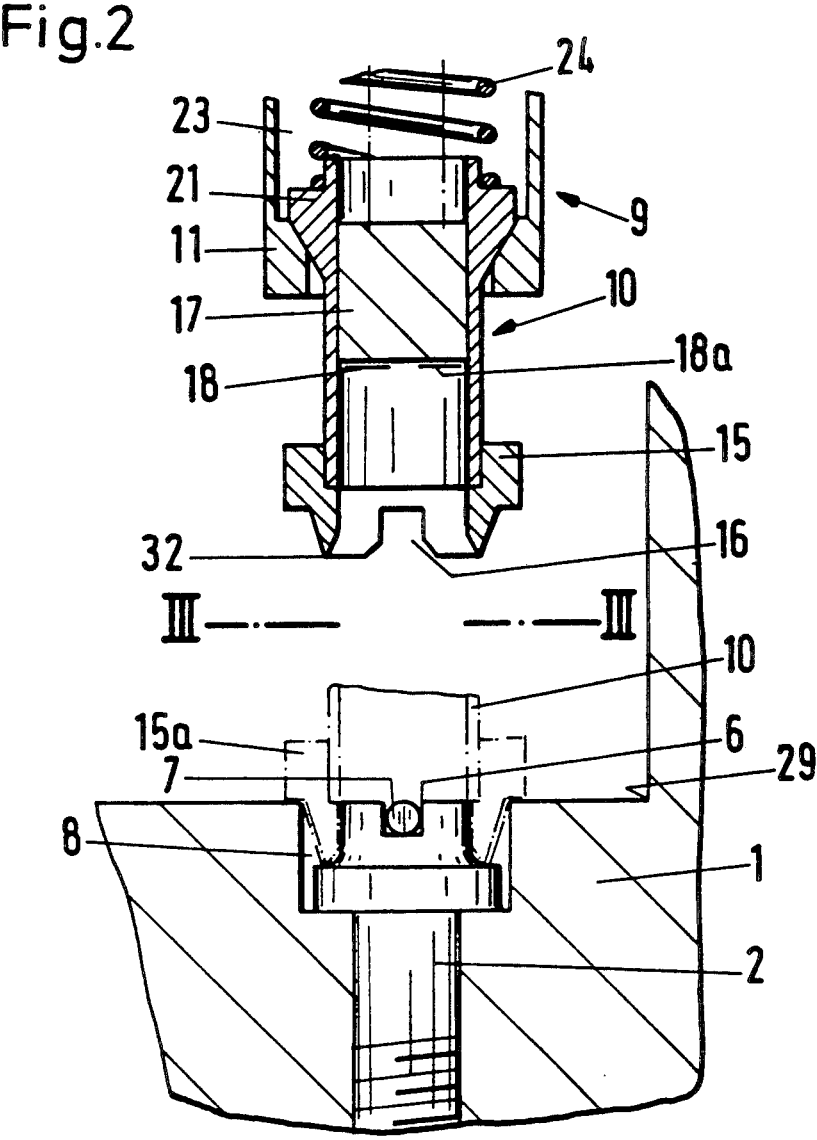
FIG. 2 is an enlarged view of a portion of FIG. 1.

The end of the centering piece 10 facing the head screw 2 has an annular adaptor 15, which is rigidly connected with the centering piece 10 as a part of the centering piece 10. The inner surface of the part of the adaptor 15 facing the screw head 5 corresponds to the contour of the screw head and its outer surface is constructed in such a way that it can be brought into the annular space 8. Furthermore, the adaptor 15 is provided with a transverse slot 16, which is able to overlap or cover and exactly fit the part of the securing pin 7 projecting into the annular space 8, as seen in FIG. 2.

A carrier 17 is embedded in the end of the centering piece 10 facing away from the adaptor 15. The carrier 17 is constructed in the shape of a stopper and accommodates two diametrically oppositely disposed ultrasonic transducers 18, 18a on the end thereof facing the head screw 2. The cross-sections of the transducers are adapted as far as possible to the shape of a particular segment 19 of the screw head 5 illustrated in FIG. 3, that is to be ultrasonically irradiated. Exciter and measuring leads 20 of the ultrasonic transducers lead out of the ultrasonic probe 9, but the further extent thereof is not represented. The end of the centering piece 10 facing away from the adaptor 15 is provided with a collar 21, which is convexly constructed and overlapped by an offset 22 of the floating holder 11. The offset 22 has a surface contacting the collar 21, in the vicinity of which the offset is constructed convexly in the same fashion. A cavity 23 formed in the floating holder 11 accommodates a compression spring 24, which comes to bear against the rear surface of the collar 21 of the centering piece 10 and against a wall 25 which forms a rear termination of the floating holder 11, in order to ensure permanent, resilient contact between the collar 21 and the offset 22. An end 26 of a piston rod 27 of the lift cylinder 12 is detachably embedded in the wall 25 of the floating holder 11 facing away from the compression spring 24. The rotary drive 13 is connected in series with the lift cylinder 12, through the interconnection of a slip clutch 28. Due to the slim construction of the probe 9 it can also be used at narrow locations, as is indicated by corners 29 of the component 1.

As soon as the ultrasonic probe 9 has been brought into the position shown in FIG. 1 by means of the slide 14, the centering piece 10 is moved in a linear fashion (along the direction of an arrow 30) by means of the floating holder 11 and the lift cylinder 12 until contact is established with the screw head 5. The rotary drive 13 then performs an additional rotary movement in the direction of an arrow 31 until the centering piece 10 with its adaptor 15 has reached a position 15a indicated in phantom in FIG. 2. In this process, the slip clutch 28 interrupts the rotary movement as soon as the transverse slot 6 has engaged with the securing pin 7. The linear movement of the centering piece 10 by the lift cylinder 12 is then further continued until the an surface 32 of the adaptor 15 comes to bear against the shouldered surface of the screw head 5, with the cradle or pendulum mounting enabling the desired centering. The ultrasonic testing takes place once this exact test position has been reached.

We claim:

1. A device for ultrasonic testing of a head screw inserted into a component, the screw having a head with an end surface, comprising an ultrasonic probe facing toward the end surface of the head of the screw, said probe having a cradle-mounted centering piece and an axis defining an axial direction, at least one ultrasonic transducer disposed in said centering piece, said centering piece having an adaptor disposed closer to the head of the screw than said at least one ultrasonic transducer, and means for moving said probe about the axis and in the axial direction of said probe for achieving a centering connection with the head of the screw.

2. The device according to claim 1, wherein the head of the screw has a securing element, and said moving means moves said adaptor into a centering connection with said securing element.

3. The device according to claim 1, including a securing element disposed in the head of the screw, said moving means moving said adaptor into a centering connection with said securing element in addition to the head of the screw.

4. The device according to claim 1, wherein said probe has a floating holder accommodating and being disposed in series with said centering piece, and said probe has a lift cylinder and a rotary drive being connected to and disposed in series with said centering piece.

5. The device according to claim 4, including a slip clutch connected between said drive and said lift cylinder for automatically interrupting rotation after said adaptor has engaged a contour of the head of the screw.

6. The device according to claim 4, wherein said centering piece has a collar facing away from the head of the screw, said floating holder overlaps said collar, said floating holder has a cavity formed therein, and including a compression spring extended between said centering piece and said floating holder in said cavity.

* * * * *